(12) United States Patent
Kravtsov et al.

(10) Patent No.: US 12,064,443 B2
(45) Date of Patent: Aug. 20, 2024

(54) COMPOSITIONS AND METHODS FOR TREATING DISEASES ASSOCIATED WITH DRUG WASHOUT DUE TO FLUID SECRETION

(71) Applicant: VANESSA RESEARCH, INC., Hamden, CT (US)

(72) Inventors: Dmitry Kravtsov, Cheshire, CT (US); Norman Gray, Hamden, CT (US)

(73) Assignee: VANESSA RESEARCH HOLDINGS, INC., Hamden, CT (US)

( * ) Notice: Subject to any disclaimer, the term of this patent is extended or adjusted under 35 U.S.C. 154(b) by 0 days.

(21) Appl. No.: 18/235,867

(22) Filed: Aug. 20, 2023

(65) Prior Publication Data
US 2023/0398136 A1   Dec. 14, 2023

Related U.S. Application Data

(63) Continuation of application No. PCT/IB2022/051492, filed on Feb. 20, 2022.

(60) Provisional application No. 63/151,485, filed on Feb. 19, 2021.

(51) Int. Cl.
| | | |
|---|---|---|
| A61K 31/7016 | (2006.01) | |
| A61K 9/06 | (2006.01) | |
| A61K 31/194 | (2006.01) | |
| A61K 31/225 | (2006.01) | |
| A61K 36/736 | (2006.01) | |
| A61K 45/06 | (2006.01) | |
| A61P 1/12 | (2006.01) | |

(52) U.S. Cl.
CPC ............ *A61K 31/7016* (2013.01); *A61K 9/06* (2013.01); *A61K 31/194* (2013.01); *A61K 31/225* (2013.01); *A61K 36/736* (2013.01); *A61K 45/06* (2013.01); *A61P 1/12* (2018.01)

(58) Field of Classification Search
None
See application file for complete search history.

(56) References Cited

FOREIGN PATENT DOCUMENTS

| CN | 107582806 A | * | 1/2018 | ......... A61K 31/7024 |
|---|---|---|---|---|
| CN | 107596370 A | * | 1/2018 | ......... A61K 31/7024 |

* cited by examiner

*Primary Examiner* — Dale R Miller
(74) *Attorney, Agent, or Firm* — Law Office of John K. Pike, PLLC (57) ABSTRACT

A composition for the treatment of diarrheal and other diseases, comprising a reaction product of one or more polyphenol compound; sucralfate; and at least one acid.

15 Claims, 6 Drawing Sheets

«COMPOSITIONS AND METHODS FOR TREATING DISEASES ASSOCIATED WITH DRUG WASHOUT DUE TO FLUID SECRETION»

COMPOSITIONS AND METHODS FOR TREATING DISEASES ASSOCIATED WITH DRUG WASHOUT DUE TO FLUID SECRETION

RELATED APPLICATIONS

This application claims the benefit of U.S. Application 63/151,485, filed Feb. 19, 2021, the entire contents of which are hereby incorporated by reference.

FIELD OF THE INVENTION

The invention relates to compositions for the treatment of diarrheal and other diseases, and methods for their use in treating diarrheal and other diseases.

BACKGROUND

Figure 1:
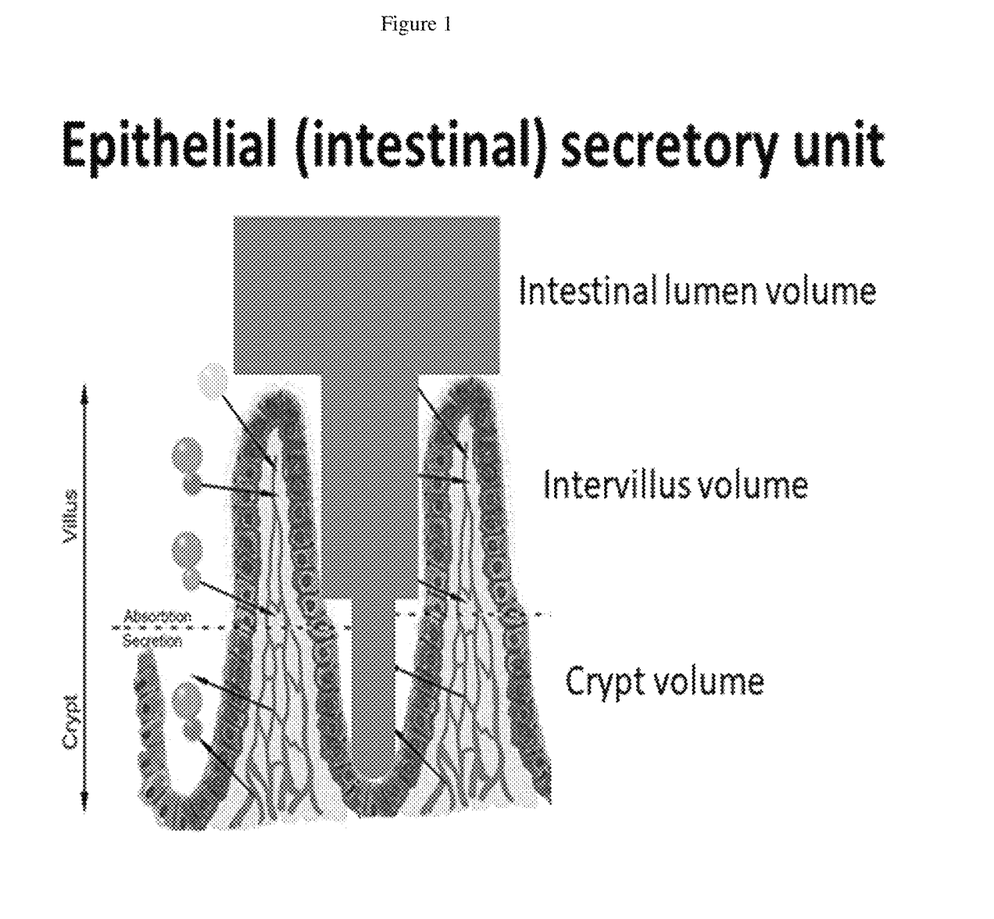
FIG. 1 presents in cross section a representation of an epithelial secretory unit, which includes the space connecting the bottom of the epithelial gland and the surface of the organ. It can be viewed or modeled as a cylinder of varying diameter (solid gray shape) limited by the epithelial cells of glands and related structures, such as epithelial villus or cilial walls as shown on the example of intestinal epithelium.

An epithelial secretory unit consists of the space connecting the bottom of the epithelial gland and the surface of the organ. It can be viewed as a cylinder of varying diameter limited by the epithelial cells of glands and related structures, such as epithelial villus as shown on the example of intestinal epithelium (grey space, FIG. 1).

Each secretory unit produces (secretes) water, electrolytes and mucus. Output from all the secretory units combines along the length of the organ. If secretion>absorption, the epithelial organ is in a so-called net secretory state, and fluid expulsion results. If secretion<absorption, the intestine is in a so-called net absorptive state, fluid expulsion does not occur, and fluid absorption ensues.

The secretion unit is overlaid by a 50-500 μm thick layer of unstirred fluid, consisting of immobile layer of mucus and water. This mucus layer is classically viewed as a protective barrier, which creates an obstacle for a drug accessing its targets.

Mucus has dual properties which are drastically different for macro- and micro-rheology of mucus. This is why mucus moves relatively slowly and traps objects larger than about 200-500 nm, while allowing free and unimpeded passage of molecules and particles smaller than a threshold of about 200 nm or 2000 Da.

In the case of orally administered drugs, which act on the luminal (apical) surface of intestinal cells forming the walls of the crypt, the active substance must diffuse from the intestinal lumen to the site of action at the bottom of secretion unit. This diffusion happens against a continuous flux of fluid from the secretion unit, the so-called "convective washout". If the convective washout is too strong, the drug cannot overcome the washout to reach the target receptor, and the desired therapeutic effect is not achieved. The problem of convective washout has been noted by others, e.g., such as described and modeled by Lin et al. in 2013.

Two parameters are important for timely diffusion of small molecules: concentration gradient and diffusion coefficient. The present inventors have calculated concentration profiles for a drug under a net absorptive state of the intestine (secretion velocity=0) and under a net secretory state of the intestine (secretion velocity=$4e^{-2}$ μl/cm$^2$). The concentration profiles vary drastically. At diffusion coefficient of $2e^{-10}$ m$^2$/s, concentration 10 μm, and time 20 min, the drug fully penetrates into the crypt in the absorptive state and does not penetrate into the crypt under secretory state. This demonstrates the effect of convective washout, i.e. when outflow of secreted fluid prevents drug penetration into the bottom of secretion unit. There are two ways to improve penetration: 1) higher diffusion coefficient, and 2) higher concentration; the diffusion coefficient having a 10× more pronounced effect.

Each intestinal epithelial secretory unit contains varying amounts of mucus in accord with the anatomical and functional property of epithelial tissue. As noted above, the layer of mucus possesses dual rheology: a highly viscous macroscopic rheology and a water-like microscopic rheology. The velocity of convective washout from the intestinal secretory unit and within such unit is dictated by the composition of the fluid contained in such unit. Poiseuille's law dictates that radius and viscosity are the critical parameters defining the flow in a pipe and pressure gradient needed to ensure the flow. If water occupies a majority of the secretory unit volume, one can expect high degree of convective washout. If mucus occupies a majority of the volume, then one can expect the slow movement with minimum convective washout.

Figure 2:
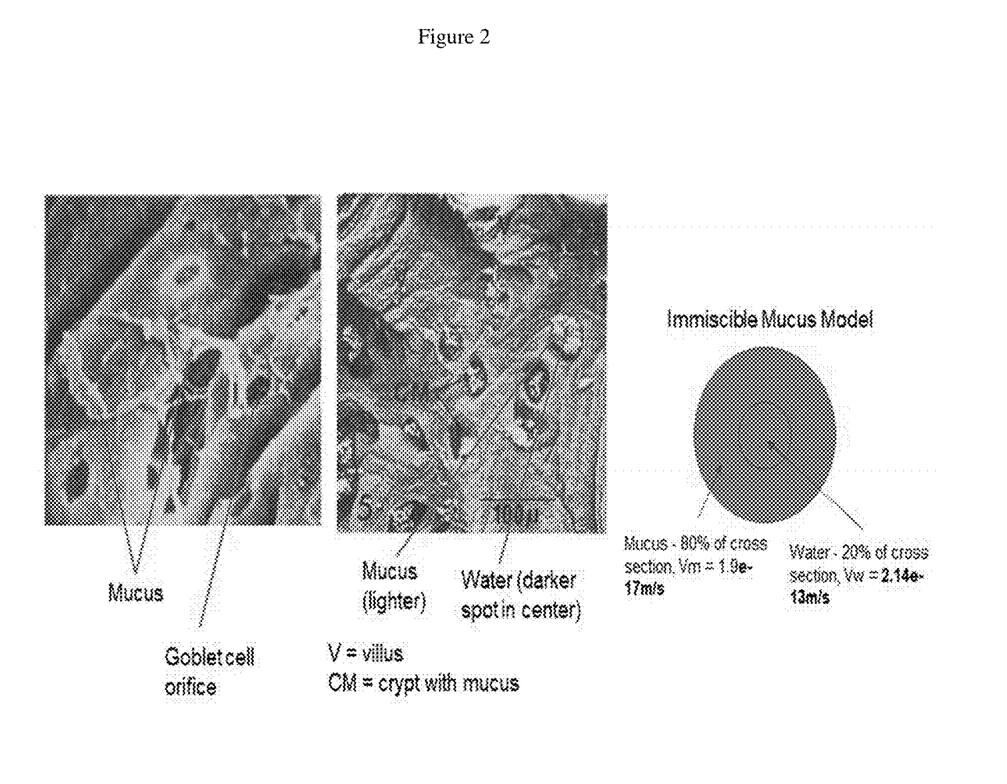
FIG. 2 presents a photomicrograph showing an intestinal epithelium, epithelial secretory unit, villus, crypt with mucus, and a model immiscible mucus.

It is not uncommon for the mucus to occupy 50% or more of the volume of secretory unit. Mucus is not miscible with water (FIG. 2). In such a case, two different flow patterns will coexist within the same secretory unit: a rapid flux for low-viscosity water component, which impedes the diffusion, and a slow flux for the viscous mucus, which is conducive for diffusion. Mucus affects the velocity of the fluid due to its macro-rheological properties, but mucus does not affect the diffusion of small molecules, behaving indistinguishable from water due to its micro-rheological properties.

For a dP of 7 Pa and identical secretory unit geometry, linear velocity for water (0.00089 Pas)=2.14E-13 m/s and velocity for mucus at (10 Pas)=1.91E-17 m/s. The inventors have determined that drug diffusion patterns corresponding to these velocities are indicative of complete penetration into the secreting crypt. Without wishing to be bound by theory, it is further believed that the outer border of the immobile fluid phase has the highest concentration of a drug, which equals the concentration of the drug dissolved in the intestinal lumen at time equals zero.

BRIEF DESCRIPTION OF THE INVENTION

The present invention solves the above problems and other problems, by providing an anti-secretory antidiarrheal drug. Other embodiments of the present invention include the means to overcome the problem of convective washout, compositions that overcome the problem of convective washout, methods of treating diseases that involve or associated with convective washout, that are indicated by or accelerated by convective washout, e.g., by secretion of epithelial cells or tissues, e.g., in the intestine. Examples are provided and confirm the efficacy of the present compositions in the case of secretion in the intestine, manifesting as severe diarrhea, such as that of cholera.

In an embodiment, a composition is provided, comprising a reaction product of:
one or more polyphenol compound;
sucralfate; and
at least one acid.

In an embodiment, and referring to the aforementioned compositions the polyphenol may be one or more of blueberry, bilberry, sloe, chokeberry, grape, grape pomace, black rose, blackcurrant, pecarin, crofelemer, Dragon's Blood (*Croton* spp.) dried form thereof, seed form thereof, juice thereof, powder form thereof, liquid form thereof, extract thereof, or combination thereof.

In an embodiment, and referring to the aforementioned compositions the polyphenol may be one or more of blueberry, bilberry, sloe, chokeberry, blackcurrant, dried form thereof, seed form thereof, juice thereof, powder form thereof, liquid form thereof, extract thereof, or combination thereof.

In an embodiment, and referring to the aforementioned compositions the polyphenol may be a mixture of sloe and blueberry, mixture of sloe and bilberry, dried form thereof, seed form thereof, juice thereof, powder form thereof, liquid form thereof, extract thereof, or combination thereof.

In an embodiment, and referring to the aforementioned compositions the polyphenol may be one or more of gallic acid, hydrolysable gallic acid, non-hydrolyzable gallic acid, condensed gallic acid, phlorotannin, cyanidin, delphinidin, petunidin, pelargonidin, peonidin, malvidin, catechin, gallocatechin, epicatechin, epigallocatechin, quercetin, tannic acid, apigenin. penta-m-digalloyl glucose, tannin, condensed tannin, gallotannic acid, gallotannin, tanninium, monomeric form thereof, polymer thereof having degree of polymerization of 1, 2 or more, glycosylated form thereof, aglycone form thereof, salt thereof, ester thereof, or combination thereof.

In an embodiment, and referring to the aforementioned compositions the polyphenol may be tannic acid, gallic acid, salt thereof, or combination thereof.

In an embodiment, and referring to the aforementioned compositions, the acid may be selected from the group consisting of citric acid, HCl, malic acid, tartaric acid, succinic acid, oxalic acid, benzoic acid, isocitric acid, quinic acid, fumaric acid, acetic acid, lactic acid, fruit acid, and combinations thereof.

In an embodiment, and referring to the aforementioned compositions, the acid may be selected from the group consisting of citric acid, malic acid, tartaric acid, succinic acid, oxalic acid, or any combination thereof.

In an embodiment, and referring to the aforementioned compositions, the acid may be selected from the group consisting of HCl, citric acid, malic acid, and combinations thereof.

In an embodiment, and referring to the aforementioned compositions, the acid/polyphenol/sucralfate weight ratio may be acid/polyphenol/sucralfate weight ratio is acid 0.0001-1:polyphenol 0.001-1:sucralfate 0.0001-1.

In an embodiment, and referring to the aforementioned compositions, the acid/polyphenol/sucralfate weight ratio may be acid 0.001-0.5:polyphenol 0.002-0.5:sucralfate 0.0001-0.5.

In an embodiment, and referring to the aforementioned compositions, the acid/polyphenol/sucralfate weight ratio may be acid 0.1-1:polyphenol 0.05-0.5:sucralfate 0.01-1.

In an embodiment, and referring to the aforementioned compositions, the compositions may further comprise an active or anti-diarrheal selected from the group consisting of loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

In an embodiment, and referring to the aforementioned compositions, the compositions may be in the form of a hydrogel.

In an embodiment, a method is provided for making the composition, comprising:
contacting one or more polyphenol compound, sucralfate, and at least one acid; and
reacting, to form a reaction product.

Referring to the aforementioned method, the polyphenol and sucralfate may optionally be contacted first with each other, and then with the acid.

In an embodiment, and referring to the aforementioned method, the sucralfate and acid may optionally be contacted first with each other, and reacted, and then contacted and reacted with the polyphenol.

In an embodiment, a method is provided for treating a diarrheal disease, comprising administering to a subject needing such treatment or at risk of needing such treatment, a composition; the composition comprising a reaction product of:
one or more polyphenol compound;
sucralfate; and
at least one acid.

In an embodiment, a composition is provided for the treatment of a diarrheal disease, comprising:
one or more polyphenol compound; and
sucralfate;
wherein the polyphenol is not extracted from green tea leaves, and does not contain catechins extracted from green tea leaves.

In an embodiment, a method is provided for treating a diarrheal disease, comprising administering to a subject needing such treatment or at risk of needing such treatment, a composition; the composition comprising a reaction product of:
one or more polyphenol compound;
sucralfate; and
at least one acid;
and at least one active or anti-diarrheal selected from the group consisting of loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

In an embodiment, a method is provided for treating secretory diarrhea, comprising administering to a subject needing such treatment or at risk of needing such treatment, a composition; the composition comprising a reaction product of:
  one or more polyphenol compound;
  sucralfate; and
  at least one acid.

In an embodiment, a composition is provided for the treatment of diarrheal disease associated with drug washout due to fluid secretion, comprising a reaction product of:
  one or more polyphenol compound;
  sucralfate;
  at least one acid:
  and at least one active or anti-diarrheal selected from the group consisting of loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

In an embodiment a method is provided for treating a diarrheal disease associated with drug washout due to fluid secretion, comprising administering to a subject needing such treatment or at risk of needing such treatment, a composition; the composition comprising a reaction product of:
  one or more polyphenol compound;
  sucralfate;
  at least one acid:
  and at least one active or anti-diarrheal selected from the group consisting of loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

DETAILED DESCRIPTION OF THE INVENTION

The present inventors have found how the mucus produced by goblet cells of epithelial tissues can be utilized to facilitate drug transport in epithelial organs, and novel compositions are provided that surprisingly and unexpectedly demonstrate effectiveness in treating diarrheal disease and other disease, in including severe secretory diarrhea. In embodiments, the diarrheal disease is associated with drug washout due to fluid secretion.

The inventors have considered that since mucus (viscoelastic hydrogel) is contributing to the volume of fluid filling the epithelial secretory unit, a favorable fluid output velocity profile can thereby exist, which may allow for efficient drug delivery if properly utilized. The inventors have found that if a drug is to act on the target receptors located on the apical domain of crypt cells, it is necessarily to either (1) significantly increase the dose of the drug in order for it to work in the background of convective washout, (2) design a drug with a higher diffusion coefficient, or (3) design a systemic drug which is not dependent on the convective washout at all. None of these choices is a good one: increasing the dose and giving drug systemically will lead to the development of side effects, and finding a molecule with a combination of desired pharmacology and high diffusion coefficient may be simply impossible.

In one embodiment, a method of drug administration is provided whereby the mucus is used as a vehicle for drug delivery in the presence of, and as the means to evade the convective washout by affixing the vehicle loaded with drug to the layer of immobile, or relatively immobile, mucus contained in the epithelial secretory unit. Drug delivery vehicle (small particle, gel, film, etc.) is immobilized by the mucus and is consequently decoupled from the convection washout, while at the same time, the released drug freely diffuses through the mucus and rapidly comes in contact with its target elements of the epithelial surface. It is desirable that the drug freely diffuse through the mucus (i.e. be <2000 Da in size) while the vehicle should be entrapped by the mucus, e.g., due to the relatively large size of the vehicle (>200 nm) or due to its mucoadhesive properties. In this regard, the use of mucus as vehicle is distinct from a traditional tablet, capsule, or slow-release preparation.

As stated above, one way to overcome the convective washout problem is to increase the concentration of the drug 100 times. Human small intestine is a pipe with the length of approximately 6 meters (5-7 m) and a diameter of about 5 cm, giving it a steady-state volume of 12 liters. 1 mM drug with Kd of 10 μm and MW of 300 g/mol in 12 liters would constitute a steady-state dose of 3.6 g. Considering stool volume in cholera reaching 100 ml/kg/day, the steady-state volume should be supplemented by the volume of stool loss, adding extra 71 per day in a 70 kg adult. Thus, the total dose of the component may approach 6 g/day in order to ensure the antidiarrheal efficiency. Obviously, this dose is very high, and significant side effects are expected to ensue from this dose.

There is an element in the above calculations which is defined by morphology of the epithelial secretory unit. Concentration of the drug is defined at the outer border of the immobile fluid phase. Anatomically, there is no distinction between the luminal content and the outer border of the immobile fluid phase. Thus, outer border of the immobile fluid phase has the highest concentration of the drug which equals the concentration of the drug dissolved in the intestinal lumen at time=zero.

If the entire amount of highly concentrated drug is attached as a layer overlaying the immobile fluid phase instead of being dissolved in the entirety of the fluid occupying the intestinal lumen, then the luminal volume is no longer a factor in the drug delivery, and the dose of the drug may be reduced significantly.

In this application a method of drug administration is provided whereby the drug is delivered as a thin coat of highly concentrated active substance covering the surface of the intestinal epithelium by adhering to the surface elements of intestinal epithelial cells, or the layer of intestinal mucus, or the immobile fluid phase covering the intestinal epithelium. Without wishing to be bound by theory, this is believed to be different from the classic idea of oral vehicle which is releasing the drug into the entire volume of intestinal content, (whether immediately or over a period of time, as active substance or nanoparticles, etc.) because it allows for up to 100 times reduction of the dose of the drug which needs to be administered to the patient.

In one aspect, a composition is provided for the treatment of diarrheal disease associated with drug washout due to fluid secretion, comprising:

at least one active or anti-diarrheal selected from the group consisting of polyphenol, loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof; and an epithelial surface- or mucus-binding, thin-film forming compound selected from the group consisting of hydrogel-forming agent, acid-modified sucralfate, mixture of sucralfate, acid-modified sucralfate, and sucrose octasulfate, sucralfate, gum, mucus-binding agent, biological adhesive, salts thereof, or combination thereof.

In embodiments, a composition is provided that includes an active or anti-diarrheal to be delivered against the convective washout, and an epithelial surface- or mucus-binding, thin-film forming compound, wherein the epithelial surface- or mucus-binding, thin-film forming compound carries the active or anti-diarrheal, binds to epithelial surface or mucus produced by the epithelial tissues, forms a thin film covering areas of mucosal membranes, and releases the active or anti-diarrheal into the mucus.

The active or anti-diarrheal is not particularly limiting. Some non-limiting examples include polyphenol, loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

A preferred embodiment of active or anti-diarrheal is polyphenol. Prior to combining the polyphenol with the thin-film forming compound, the polyphenol may be in the form of a liquid extract, suspension, or dispersion, or it may be in the form of a dried powder, or any combination thereof.

Suitable examples of polyphenols may be found in U.S. Pub. No. 2018/0338932, published Nov. 29, 2018 and U.S. Pub. No. 2021/0008028, both to the present Applicant, published Jan. 14, 2021, the entire contents of which are hereby incorporated by reference for all combinations.

The polyphenol is not particularly limited. The polyphenol is a synthetic or naturally occurring polyphenol rich in —OH groups and having antiproliferative properties and/or inhibitory activity against ion and water transport proteins.

In embodiments, the polyphenol is one or more of plant-derived, botanical, anthocyanoside, anthocyanidin, proanthocyanidin, tannin, or a combination thereof.

In embodiments, the polyphenol is one or more of blueberry, bilberry, sloe, chokeberry, grape, grape pomace, black rose, blackcurrant, pecarin, crofelemer, Dragon's Blood (*Croton* spp.) dried form thereof, seed form thereof, juice thereof, powder form thereof, liquid form thereof, extract thereof, or combination thereof. In embodiments, the polyphenol is one or more of blueberry, bilberry, sloe, chokeberry, blackcurrant, or combination thereof. In a preferred embodiment, the polyphenol is a mixture of sloe and blueberry, or mixture of sloe and bilberry. More preferred is a mixture of sloe and blueberry.

In embodiments, the polyphenol is one or more of gallic acid, hydrolysable gallic acid, non-hydrolyzable gallic acid, condensed gallic acid, phlorotannin, cyanidin, delphinidin, petunidin, pelargonidin, peonidin, malvidin, catechin, gallocatechin, epicatechin, epigallocatechin, quercetin, tannic acid, apigenin. penta-m-digalloyl glucose, tannin, condensed tannin, gallotannic acid, gallotannin, tanninium, monomeric form thereof, polymer thereof having degree of polymerization of 1, 2 or more, glycosylated form thereof, aglycone form thereof, salt thereof, ester thereof, or combination thereof. In a preferred embodiment, the polyphenol is cyanidin, delphinidin, catechin, epicatechin, epicatechin gallate, tannic acid, gallic acid, glycosylated form thereof, aglycone form thereof, polymer thereof, or combinations thereof. In another preferred embodiment, the polyphenol is tannic acid, gallic acid, salt thereof, or combination thereof.

If the polyphenol is in liquid extract form, the solvent is not particularly limiting. Preferred solvents include ethanol, water, or a combination thereof. The polyphenol concentration, or Total Polyphenol Index (TPI) established by FC method, in the liquid extract is preferably 15 mg/100 ml or higher, although lower concentrations are also contemplated herein. For example, for liquid extracts, the TPI can range from 0.5 to 50 mg/mL and higher, including 0.8-4.5 mg/mL, 2.0-4.5 mg/mL, 2.5-4.0 mg/mL, 2.8-4.5 mg/mL, 5-30 mg/mL, 10-25 mg/mL, 15 mg/mL, 0.5 to 100 mg/mL, and higher.

If the polyphenol is in solid form, such as a dried powder or dried liquid extract, the TPI is preferably 10 mg/g or higher 0.1-999.9 mg/g, 0.1-2 mg/g, 0.5-3.5 mg/g, 0.5-15 mg/g, 1-500 mg/g, 5-400 mg/g, 10-300 mg/g, 20-200 mg/g, 325-500 mg/g, 300-450 mg/g, and higher. Depending on context, the term, "Polyphenol extract" may refer to the liquid form or the solid form. In a preferred embodiment, the term refers to the solid form herein.

In one embodiment, in addition to polyphenol, the composition may additionally include other active agents. Some non-limiting examples include loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

The epithelial surface- or mucus-binding, thin-film forming compound is not particularly limiting. Some non-limiting examples include hydrogel-forming agent, acid-modified sucralfate, mixture of sucralfate, acid-modified sucralfate, and sucrose octasulfate, sucralfate, gum, mucus-binding agent, biological adhesive, salts thereof, or combination thereof. In embodiments, the epithelial surface- or mucus-binding, thin-film forming compound is chosen from sucralfate, acid-modified sucralfate, or mixture of sucralfate, acid-modified sucralfate, and sucrose octasulfate, and salts thereof. Most preferable is sucralfate and acid-modified sucralfate.

Sucralfate ($C_{12}H_{54}Al_{16}O_{75}S_8$), has the following chemical structure:

Sucralfate is poorly soluble in water. Sucrose octasulfate-potassium salt, on the other hand, is freely soluble in water. When administered to the acidic environment (such as stomach), sucralfate loses $Al(OH)_3$ as a function of acid concentration, transitioning from solid to hydrogel to liquid as a function of the number of lost $Al(OH)_3$ moieties. For best clinical efficacy of sucralfate, it is best administered orally to react with stomach acid to maximize its beneficial enterocoating properties.

The acid-modified sucralfate results from treatment of sucralfate with one or more acids. Sucralfate is a complex of sucrose and aluminum hydroxide that forms a viscous hydrogel to loose hydrogel to liquid viscous paste in aqueous acidic media. In an acidic environment (pH<4), sucralfate undergoes cross-linking and polymerization, which is believed to be at least in part from the stripping of $Al(OH)_3$ from $SO_3^-$ groups, hydrogen bonding among the one or more of hydroxy-hydrates and hydrous oxides of aluminum, $Al(OH)_n(H_2O)_{5-n}^{+(3-n)}$ wherein n is 1-3. For the reaction product, on combining with the polyphenol, it is believed that the —OH groups on the polyphenol participate in the hydrogen bonding (or coordinated bonding, chelated bonding, or (unlikely) covalent bonding) network and are thus entrained in the acid-modified sucralfate, to further crosslink the hydrogel network. The sucralfate, acid, and polyphenol may be contacted in any order, and optionally dried and/or reconstituted with water and/or ethanol, to result in the reaction product, which may further include one or more of sucralfate, sucrose octasulfate, sucrose octasulfate salt, mixed salt of sucralfate, hydroxy-hydrates and hydrous oxides of aluminum, other aluminum salt, and combinations thereof as reaction products.

It is also contemplated that the composition could be arrived at by starting with sucrose octasulfate, or sucrose octasulfate salt (and not sucralfate), and adding an Al(III) salt, and a polyphenol, and adjusting the pH.

Sucralfate upon reaction with acid and polyphenol is believed to act as a hydrogel, saturated with the antisecretory polyphenol, and the resulting composition coats intestinal epithelial secretory units as a thin layer without the need to dissolve in the intestinal lumen; binding polyphenols to the immobile mucus in the units and in doing so allowing the polyphenol to escape the effect of convective washout, diffuse into the intestinal crypts, and suppress $Cl^-$ and water secretion by intestinal cells.

In one embodiment, the sucralfate and polyphenol are mixed together, and the acid is added later. In one embodiment, the acid may originate in the stomach or gastric tract, wherein the reaction takes place. In another embodiment, the sucralfate and acid are mixed together, and the polyphenol is added later. In another embodiment, the sucralfate, polyphenol, and acid are mixed together at substantially the same time.

By controlling concentration of acid in solution or in the solid we can achieve a desired chemical composition and physical/chemical state of sucralfate from solid to viscous hydrogel to loose hydrogel to liquid.

By adjusting the ratios between acid, sucralfate and polyphenols, formulas are achieved with various solubility in water, ranging from insoluble to hydrogel to fully soluble.

The acid is not particularly limiting and may, for example, be chosen from citric acid, HCl, malic acid, tartaric acid, succinic acid, oxalic acid, benzoic acid, isocitric acid, quinic acid, fumaric acid, acetic acid, lactic acid, fruit acid, or any combination thereof. In embodiments, the acid is chosen from citric acid, HCl, malic acid, tartaric acid, succinic acid, oxalic acid, isocitric acid, fumaric acid, or any combination thereof. In embodiments, the acid is chosen from citric acid, malic acid, tartaric acid, succinic acid, oxalic acid, isocitric acid, or any combination thereof. In embodiments, the acid is chosen from citric acid, malic acid, tartaric acid, succinic acid, oxalic acid, or any combination thereof. In embodiments, the acid is HCl, citric acid, malic acid, or combinations thereof.

The relative amounts of active or anti-diarrheal and epithelial surface- or mucus-binding, thin-film forming compound are not particularly limiting. For example, they may be present in w/w ratios ranging from 1:100 to 100:1, inclusive, which includes any of 1:100, 10:90, 20:80, 30:70, 40:60, 50:50, 60:40, 70:30, 80:20, 90:10, and 100:1 or any value or subrange therebetween.

W/w/w ratios for the polyphenol, sucralfate and acid are not particularly limiting, and may suitably be adjusted according to desired formulation. For example, in any composition herein, the acid/polyphenol/sucralfate weight ratio may be acid 0.0001-1:polyphenol 0.001-1:sucralfate 0.0001-1; acid 0.001-0.5:polyphenol 0.002-0.5:sucralfate 0.0001-0.5; acid 0.05-0.25:polyphenol 0.02-0.1 sucralfate 0.02-0.25; and acid 0.1-1:polyphenol 0.05-0.5:sucralfate 0.01-1; and all values, combinations and subranges therebetween.

In embodiments, sucralfate (powder) mixed with polyphenol (powder) and reconstituted in acid solution (i.e. hydrochloric acid, citric acid, malic acid, acetic acid, etc.) will form a water-insoluble hydrogel saturated with polyphenols. Hydrogel viscosity can be adjusted by changing acid concentration. VR-AD-1005, hydrogel mixed with polyphenols as described herein, is an example.

The hydrogel is stable for up to 12 hours with agitation; after that, or if mixed to uniformity and allowed to sit still for more than 10 minutes, liquid hydrogel re-polymerizes into a solid paste. Re-polymerization is facilitated by drying and cooling.

By adjusting the type of polyphenol, formulas are achieved with various solubility in water, ranging from insoluble to hydrogel to fully soluble and various in vivo efficacy.

Formulas having hydrogel structure upon reconstitution are most beneficial for attachment to gastrointestinal mucosal membranes and countering convective washout.

Optional ingredients include one or more of sucrose, sodium, potassium, magnesium, zinc, calcium, selenium, bismuth, organic acid, salts thereof, may be present. In one embodiment, the composition does not contain sucrose. In another embodiment, the composition does not contain any sugar. In one embodiment, the polyphenol is not extracted from green tea leaves, and does not contain catechins extracted from green tea leaves.

One embodiment is a combination of sucralfate and polyphenol combination extracted from the mixture of blueberry and sloe berry.

One embodiment of a composition for treating diarrhea includes polyphenol, sucralfate, and citric acid.

Other exemplary compositions and methods are described below:

Combining polyphenol (sloe-berry and blueberry extraction) and sucralfate.

A. Solid-solid formulation. For solid-solid mixing, 1:1 w/w or 1:1:1 w/w/w is acceptable, but other ratios are contemplated.

1. Dry sloe berry, blueberry or mixed-berry liquid polyphenol-rich extracts into fine powder. Mix obtained powder with sucralfate. Encapsulate or compress into a pill while following applicable standard protocols and procedures.

2. Dry sloe berry, blueberry, or mixed-berry liquid polyphenol-rich extracts into fine powder. Mix obtained powder with sucralfate and citric acid. Encapsulate or compress into a pill while following applicable standard protocols and procedures.

B. Liquid-solid mixing. For liquid-solid mixing, liquid extract to sucralfate range of working ratios is 1:3-1:10 v/w (ml/g); in alcohol steps: (liquid extract+sucralfate) to alcohol: 1:1 v/v ((liquid extract+sucralfate):alcohol) to obtain a gel; 1:10 v/v 10 parts alcohol and 1 part polyphenol/sucralfate mixture ((liquid extract+sucralfate):alcohol) to obtain a solid.

1. Mix liquid polyphenol-rich extract with sucralfate while heating. 40° C. is recommended; do not exceed 100° C. Stir for 15 minutes. Let stand without stirring at room temperature for 1 hour. Decant supernatant and collect sediment (gel). Dry and pulverize sediment and collect the resulting powder. Incapsulate or compress powder into a pill while following applicable standard protocols and procedures.

2. Acidify liquid sloe berry, blueberry or mixed extract with citric acid to pH range between pH2 and pH3; Mix liquid polyphenol-rich extract with sucralfate while heating. 40° C. is recommended; do not exceed 100° C. Stir for 15 minutes. Let stand without stirring at room temperature for 1 hour. Decant supernatant and collect sediment (gel). Dry, pulverize and collect the sediment. Yield is improved significantly over Sequence 1.

3. Acidify liquid sloe berry, blueberry or mixed extract with citric acid to pH range between pH2 and pH3; Mix liquid polyphenol-rich extract with sucralfate while heating. 40° C. is recommended; do not exceed 100° C. Stir for 15 minutes. Add ethanol at 1:1 v/v ratio and mix to uniformity. Allow for precipitation to form by incubating without mixing for at least 1 hour at room temperature; best precipitation observed after overnight incubation at 4° C. Decant supernatant and collect sediment (gel). Dry the sediment, pulverize and collect the resulting powder. Yield is improved significantly over Sequence 2.

4. Acidify liquid sloe berry, blueberry or mixed extract with citric acid to pH range between pH2 and pH3; Mix liquid polyphenol-rich extract with sucralfate while heating. 40° C. is recommended; do not exceed 100° C. Stir for 15 minutes. Add ethanol at 10:1 v/v ratio (10 parts ethanol and 1 part polyphenol/sucralfate mixture). Allow for precipitation to form by incubating without mixing for at least 3 hours at room temperature. Unlike the previous sequences, precipitate is not a gel but is a 100% brittle solid. Decant ethanol and collect the solid, remove residual alcohol (i.e. by evaporation), pulverize and collect the resulting powder. Yield is improved significantly over Sequence 3. In addition, there is no need for drying the gel and the entire volume of extract/sucralfate is converted into the solid.

In one embodiment, the subject is a mammal. In one embodiment, the subject is a human.

Indications include treatment of any diarrheal disease with increased secretion in human or animal subjects; treatment of other diseases of epithelial organs where drug penetration into the glands against active secretion is also contemplated.

The present invention may be suitably utilized to treat both human infectious and human non-infectious diarrhea. Human infectious diarrhea which may be treated by the present invention is not particularly limited and may include, for example, bacterial and viral infectious diarrhea. Some non-limiting examples of bacterial infectious diarrhea include those due to *Vibrio* spp., e.g. *Vibrio cholera, Escherichia coli, Shigella* spp., *Salmonella* spp., *Campylobacter* spp., *Staphylococcus* spp., *Yersinia* spp., *Pseudomonas* spp., *Klebsiella* spp., *Aeromonas* spp., *Clostridium* spp., e.g. *Clostridium difficile*, food poisoning and toxin-mediated diarrhea (e.g., cholera toxin, heat-stable enterotoxin, heat-liable enterotoxin, shiga-toxins, cytotoxins etc.) or any combination thereof. Some non-limiting examples of viral infectious diarrhea include those due to Rotoviral diarrhea, Noroviral diarrhea, Parvoviral diarrhea, Adenoviral diarrhea, Astroviral diarrhea, Toroviral diarrhea, Calciviral diarrhea, Picobirnaviral diarrhea, Coronaviral diarrhea, Pestiviral diarrhea, and HIV diarrhea, or any combination thereof. Some non-limiting examples of human non-infectious diarrheal disease include inflammatory bowel disease, irritable bowel syndrome, Congenital diarrhea (congenital chloride diarrhea, congenital sodium diarrhea, microvillus inclusion disease, tufting enteropathy, primary biliary acid malabsorption among others), drug-related diarrhea, diarrhea due to chemo- or radiotherapy-induced mucositis, other diarrheal diseases, or any combination thereof.

The present invention may be suitably utilized to treat animal infectious diarrhea, such as of bacterial or viral, or non-infectious diarrhea. Some non-limiting examples of these include Calf scouring, bovine viral diarrhea, other enteric pathogens known to cause calf diarrhea (i.e., bovine rotavirus (BRV), bovine coronavirus (BCoV), bovine viral diarrhea virus, *Salmonella* (*S.*) *enterica*, *Escherichia* (*E.*) *coli*, *Clostridium* (*C.*) *perfringens*, and *Cryptosporidium* (*C.*) *parvum*) along with newly emerging enteric pathogens such as bovine torovirus (BToV) and caliciviruses (bovine norovirus (BNoV) and Nebovirus, Transmissible gastroenteritis (TGE and Porcine Epidemic Diarrhea) diarrhea of piglets under 3 weeks of age; *Salmonellosis* diarrhea in weaned pigs, swine diarrhea, Rotavirus, cryptosporidiosis, *Brachyspira hyodysenteriae* and *Escherichia coli* in pigs.

Generally, pharmaceutical compositions contain the active compound in an effective amount to achieve their intended purpose. In one embodiment, a therapeutically effective amount means an amount effective to inhibit development or progression of, or eliminate a diarrheal disease in the subject being treated. Determination of the effective amounts is within the capability of those skilled in the art in light of the description provided herein. Therapeutically effective doses may be administered alone or as adjunctive therapy in combination with other treatments.

The compositions may be administered in the form of solid, liquid, paste, emulsion, suspension or dispersion, and the like, as needed. If liquid, paste, emulsion, suspension or dispersion, the fluid can be water, saline, ethanol, other physiological carrier, or combinations thereof, So long as it does not detract from the intended effect or depart from the teachings herein, the compositions may be formulated in conventional manner using one or more physiologically acceptable carriers, excipients and auxiliaries that facilitate processing of the compounds into preparations, which can be used pharmaceutically. Proper formulation may be dependent upon the route of administration chosen, which is within the capability of those skilled in the art in light of the description provided herein.

The dosage amounts, frequency and treatment regimen are within the capability of those skilled in the art in light of the description provided herein.

Suitable routes of administration which are not intended to be limiting may include, for example, oral, rectal, intestinal, with oral being preferred. Other routes are within the capability of those skilled in the art in light of the description provided herein.

The use of the word "a" or "an" when used in conjunction with the term "comprising" in the claims and/or the specification may mean "one," but it is also consistent with the meaning of "one or more," "at least one," and "one or more than one."

The term, "about" is used to indicate that a value includes the standard deviation of error.

EXAMPLES

Extraction Methods

Extraction experiments were conducted with the use of several solvents known to elute and extract polyphenols. Acetone, methanol, ethanol and water, and combinations of thereof, were tested as extractants. The blueberries were purchased in the form of fresh (Importaciones Samanes, Navarra, Spain), frozen (StopandShop, Hamden, CT, USA), or dried-powdered fruits (NutriSeed, London, UK). Sloe berries and powder were purchased from DZ Licores (DZ Licores, Dicsatillo, Spain) and Importaciones Samanes, Navarra, Spain. Chokeberries were purchased from Amazon.com (Amazon, Seattle, WA, USA). After extraction, the total polyphenolic content in the mixture was determined by well-known Folin-Ciocalteu (FC) colorimetric method. The highest yield of polyphenols was observed when using the following two methods.

Method A.

Fresh or freshly frozen fruit mixtures were combined with 96% beet alcohol (DZ Licores) as 50/50 v/v ratio. Fruit mixture consisted of a pre-weighed combination of 50% sloe berries, 49% blueberries and 1% chokeberries as w/w ratio. After adding alcohol, the extraction mixture was incubated in the dark with periodic agitation for 90 days, followed by separation and collection of the liquid phase. Residual alcohol was evaporated from the extract, and the aqueous phase was studied for the concentration of the total polyphenols by FC method. Water in the reaction came from the berries since it is the main constituent of fresh and freshly frozen fruits, comprising up to 90% of the total weight of the fruits.

Such extraction method yielded total polyphenol concentrations in the mixtures up to 15 mg/ml of extract.

It was found that the main factors negatively affecting the yield were exposure to the light and heating the mixture to above 40° C. Similar extractions with acetone or methanol were less efficient.

To further increase the yield of polyphenols, the inventors considered that the limiting factors for the extraction were the water content in the fresh fruits and specific percentage of the ethyl alcohol in the reaction.

Method B.

To improve the control over the amount of water in the extraction reaction dried powdered fruits were used. Of all powders tested, freeze-dried berries demonstrated superiority as to the yield of the polyphenols in the extracts. Several w/w ratios of berry powders were tested, and the 50/50 w/w ratio of blueberry and sloe berry was found as the most efficient overall, however, the weight percent of each of the berries can vary significantly from 5 to 95% without much loss of the polyphenol concentration in the resulting extract. An aqueous ethyl alcohol (food grade) was used as extractant in the range of concentration from 95% alcohol to pure water. Extraction reactions were set up in the 1:3 v/v ratio of berry powder to extractant. Reactions were conducted in the dark for 1-2 hours at room temperature with continuous agitation. Further increase in the reaction time had diminishing return on the reaction efficiency. After incubation, liquid phase was separated from the reactions and collected. Alcohol was removed from the liquid phase by evaporation. Reaction temperature was controlled during all phases in order not to exceed 40° C. The yield of polyphenols was measured by FC method.

This extraction method significantly increased the concentration of polyphenols to 30 mg/ml of the extract. Extraction efficiency increased with increasing the alcohol percentage, reaching the peak between 50% and 70% v/v alcohol, after which efficiency began declining again, reaching the minimum at 95% alcohol.

The extracts were further subjected to the testing in mouse models of secretory diarrhea as follows: An extract from the 1:1 w/w mixture of blueberries and sloe berries was subjected to testing in the intestinal secretion mouse models as below. All batches of extracts that we used in the experiments were normalized to 15 mg/ml total polyphenol concentration, and are further referred to as "polyphenol extract".

Experimental Procedures

Fasting of Mice: Experimental C57/B16 mice between 20-25 g were chosen for the following experiment. Mice masses were recorded. Mice were fasted overnight in separate cages containing one plastic red hut and allowed free access to water. No bedding was present within each cage and poop pellets were removed with forceps when possible. Ambient temperature of the cage was maintained at 65-75° F. via placing a heating pad under the cages.

Gavage of Mice: Mice were manually restrained by scuffing. Mice were force fed with 200 μl of CTx (0.05 ug/ul) in 7% V/V $NaHCO_3$ PBS via an oral gavage needle attached to a 1 ml syringe. Two sheets of paper towel bedding were placed in each mouse cage. Mice had free access to water and a plastic red hut. Thirty minutes after gavage of mice with CTx, mice were manually restrained by scruffing and the test variable or control (vehicle buffer) was gavaged. One hour after CTx gavage, mice were restrained by scruffing, and the test variable was gavaged again. Solutions were allowed to incubate in the mice for five hours.

Excision of small intestine and measuring results: Mass of mice prior to surgery were recorded. Mice were euthanized via decapitation. Mice were secured to a flat surface in the supine position with masking tape. A small superficial transverse incision (1-2 cm) was made in the lower abdomen (abdominal muscle was not cut). A longitudinal incision was made from the lower abdomen rostrally without cutting abdominal muscles. Skin was separated from the musically layer below with the use of forceps. This was repeated for the abdominal muscle to allow access to the peritoneum. The abdominal muscles were pulled vertically using forceps prior to cuts to avoid puncturing of the intestine. Hydration of the small intestine was maintained throughout the procedure using PBS administered superficially via a dropper. The small intestine was ligated with a double stitched silk sutures immediately following the pyloric sphincter and before the cecum. The small intestine was cut prior to the first ligation and immediately following the cecum. Mesentery and all tissue connecting small intestine was cut using scissors prior to the removal of the small intestine from the abdomen. Caution was taken to remove all connective tissue from the small intestine prior to removal as to prevent pulling and, thereby, lengthening of the intestine. The small intestine was laid on a non-absorbable placement mat in a fashion to minimize lengthening of the intestine. This included laying one side of the intestine on the mat and then placing the intestine down in a straight line without pulling of the intestine. If the intestine was not straight then the intestine was pushed into a straight line using forceps without pinching of the intestine. Length of the intestine from the first to second suture was determined using the metric system. All remaining connective tissue was removed with the use of forceps and scissors. The mass of the intestine was recorded. The mass of the small intestine was divided by the length of the small intestine. Each population per variable was averaged. An unpaired student's T-test was used to determine significance in differences between the drug variable and the control population on a 95% confidence interval.

Cholera was used as a model for a larger group of acute watery infectious diarrheas due to the shared mechanism of inducing the watery bowel movements. Microorganisms which cause cholera, traveler's diarrhea, viral diarrhea and other diarrheal diseases with secretory component have one significant element in common: they all force cells of the intestine to produce enormous quantities of chloride into the intestinal opening. Chloride osmotically draws water into the intestine, and diarrhea with convective washout ensures. This mechanism is general and not specific to a single pathogen; rather, it covers an entire subgroup of diarrheal disorders collectively known as watery (secretory) diarrheas. The present invention is advantageous because it is designed to combat the convective washout problem and works as oral medication irrespective of the volume of stool output even in the worst cases of watery diarrhea, which is a significant limitation of the current treatment options.

Paramount to the pathology of cholera are two key features—diarrhea and the mortality. The results presented herein show that the present invention desirably and unexpectedly improves both.

Preparation of Substances for Gavage:
Materials:

| Chemical Name | Manufacturer |
| --- | --- |
| Sucralfate | Spectrum |
| Hydrochloric Acid (1N) | Sigma-Aldrich |
| Ethanol (95%) | Graves |
| Distilled Water | Vanessa Research |

Example 1

1. Add 200 mL of distilled water to a 1,000 mL side arm Erlenmeyer flask with a magnetic stirring bar and place on hotplate.
2. Add 20 grams of sucralfate to the side arm Erlenmeyer flask while stirring with slight heat.
3. Add 200 mL of 1N HCl to the side arm Erlenmeyer flask while stirring and with slight heat.
a. Cover openings of flask with aluminum foil.
4. Incubate flask with aggressive stirring and slight heat for 1 hour.
a. After one hour a paste like gel should be visible on the bottom of the flask.
5. Add 400 mL of 95% EtOH to the side arm Erlenmeyer flask while stirring.
6. Incubate flask while stirring for 45 minutes.
7. Decant supernatant of side arm Erlenmeyer flask.
8. Perform three wash steps with 100 mL 95% EtOH or 1:1 95% EtOH/$H_2O$
9. Vacuum dry paste formed at bottom of side arm Erlenmeyer flask until flakes form.
10. Scrape bottom of flask using a serological pipette tip.
11. Use a mortar and pestle to grind flakes into a fine powder.
12. Weight powder and calculate percent yield.
a. Typically, percent yield is 30% of original reactant.
13. Mix the resulting powder with liquid polyphenol-rich extract (sloe and blueberry), stir until dissolved, to thereby prepare an exemplary composition, VR-AD-1005, and administer to the animals as above.

*Decanted supernatant can be incubated in a side arm Erlenmeyer flask for one week then dried via vacuum filtration to increase percent yield*

Example 2

Powders of anhydrous citric acid (Fisher chemical, USP grade, CAS 77-92-9), polyphenol (tannic acid, Sigma Aldrich) and sucralfate (Spectrum chemical) were mixed using weight/weight ratios where citric acid may be present in the ratio from 0.01 to 1 by weight; tannic acid may be present in the ratio from 0.001 to 1 by weight and sucralfate may be present in the ratio from 0.01 to 1 by weight.

Specifically, mixtures were tested in the following ratios:
Citric acid/tannic acid/sucralfate as follows (here, in parts by weight):
0.12/0.05/0.1
0.12/0.01/0.1
0.2/0.1/1
0.25/0.03/1
0.25/0.04/1
0.25/0.05/1
0.25/0.06/1
0.25/0.07/1
0.25/0.08/1
0.25/0.09/1
0.26/0.2/1
0.26/0.02/1
0.26/0.3/1
0.26/1/1
0.3/0.02/1
0.3/0.06/1
0.3/0.1/1
0.4/0.02/1
0.4/0.06/1
0.4/0.1/1
0.5/0.03/1
0.5/0.04/1
0.5/0.05/1
0.5/0.06/1
0.5/0.07/1

0.5/0.08/1
0.5/0.09/1
0.5/0.1/1
1/0.8/0.83
1/0.4/0.83

Ingredients were dissolved in water and stirred at room temperature for 2 hours on average (30 min-overnight). The resulting liquid/gel/paste was collected and dried at room temperature and normal atmospheric pressure until fully dry into an amorphous solid (increase in the sucralfate content, heating and alcohol facilitate solidification and hardening), after which it was ground into a powder in a porcelain mortar. Powder was not hygroscopic and thus it was collected and stored in the closed tube at 4° C. without any additional precautions.

Ground powder can be resuspended, gelled or dissolved in water as follows:
- 0.25/0.03/1 Dissolved at 100 mg/ml in water, forms poorly pipettable gel at the bottom
- 0.25/0.09/1 Dissolved at 100 mg/ml in water, same as above
- 0.5/0.03/1 Dissolved at 100 mg/ml in water, dissolves, forms slurry
- 0.5/0.1/1 Dissolved at 100 mg/ml in water, dissolves, forms more slurry than above.
- 1/0.08/0.83 Dissolved at 100 mg/ml in water: dissolves completely, making transparent yellowish solution with pH 2.3.

Example 3

Powders of anhydrous citric acid (Fisher chemical, USP grade, CAS 77-92-9), polyphenol (dried sloe berry extract, Zoco Pharmaceuticals) and sucralfate (Spectrum chemical) were mixed in the weight/weight ratio as below:

Citric acid/sloe berry extract/sucralfate (here, in parts by weight)
0.12/0.12/1
0.12/0.12/0.5
0.12/0.1/1
0.12/0.1/0.3
0.12/0.05/1
0.12/0.01/1
0.12/0.01/0.5
0.12/0.05/1
0.12/0.015/0.3
0.12/0.025/0.3
0.12/0.05/0.3
0.12/0.05/0.1
0.12/0.05/0.5

Ingredients were dissolved in water and stirred at room temperature for 2 hours on average (30 min-overnight). The resultant opaque gel was collected and dried at room temperature and normal atmospheric pressure until fully dry (increase in sucralfate content, heating and alcohol facilitate solidification), after which it was ground into a powder in a porcelain mortar. Powder was not hygroscopic and thus it was collected and stored in the closed tube at 4° C. without further precautions.

Ground powder can be resuspended, gelled or dissolved in water.

Example 4

Powders of anhydrous citric acid (Fisher chemical, USP grade, CAS 77-92-9), polyphenol (dried sloe berry extract, Zoco Pharmaceuticals) and sucralfate (Spectrum chemical) were mixed in the weight/weight ratio as below:

Citric acid/sloe berry extract/sucralfate
0.12/0.12/1.1
0.05/0.4/1

Ingredients were dissolved in water and stirred at room temperature for 5-10 minutes until gelled. The resultant opaque gel can be administered for treatment of diarrheal disease as in one of the examples below.

Example 5

The above compositions in Examples 2-4 were prepared (acid/polyphenol/sucralfate) in the form of solid powders, and are not contacted with water prior to administration.

Example 6

Figure 3:
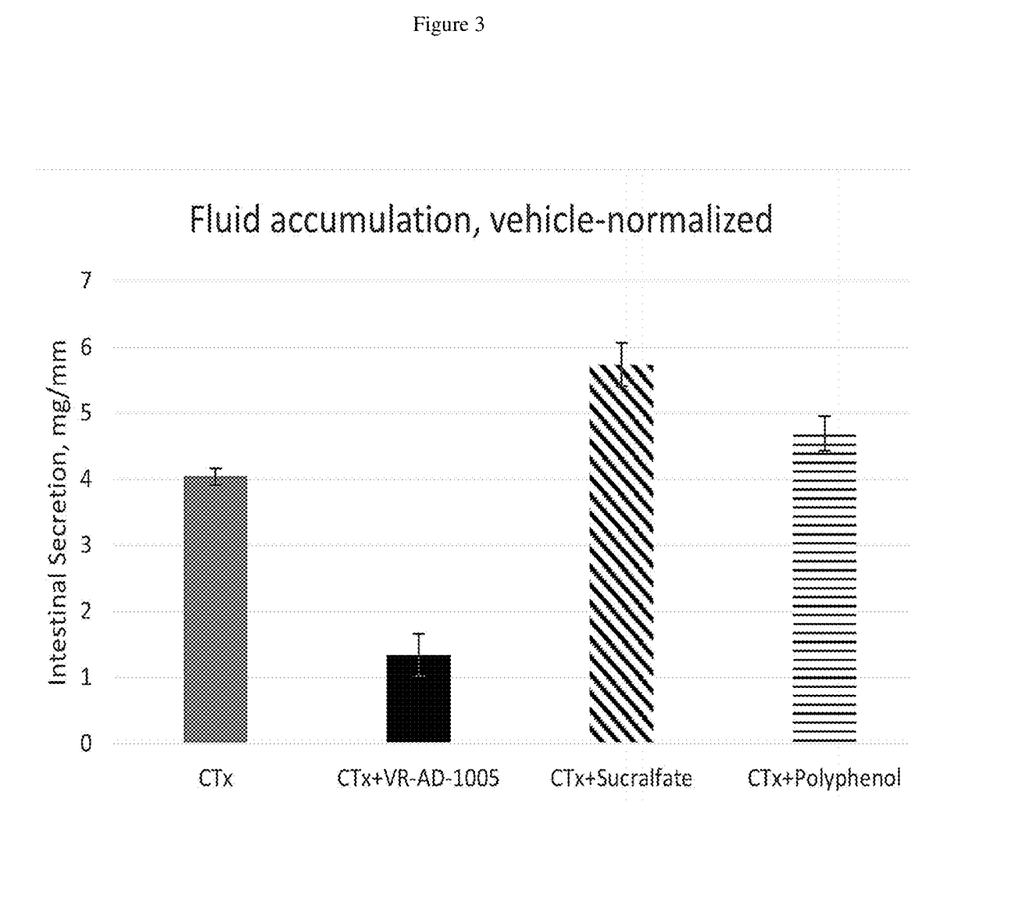
FIG. 3 presents fluid accumulation data in mice upon Cholera toxin (CTx) challenge and treatment with an exemplary composition (VR-AD-1005) and comparative compositions sucralfate and polyphenol alone. The exemplary composition significantly reduces small intestine secretion upon CTx challenge compared to the comparative compositions. This is completely unexpected and surprising.
Figure 4:
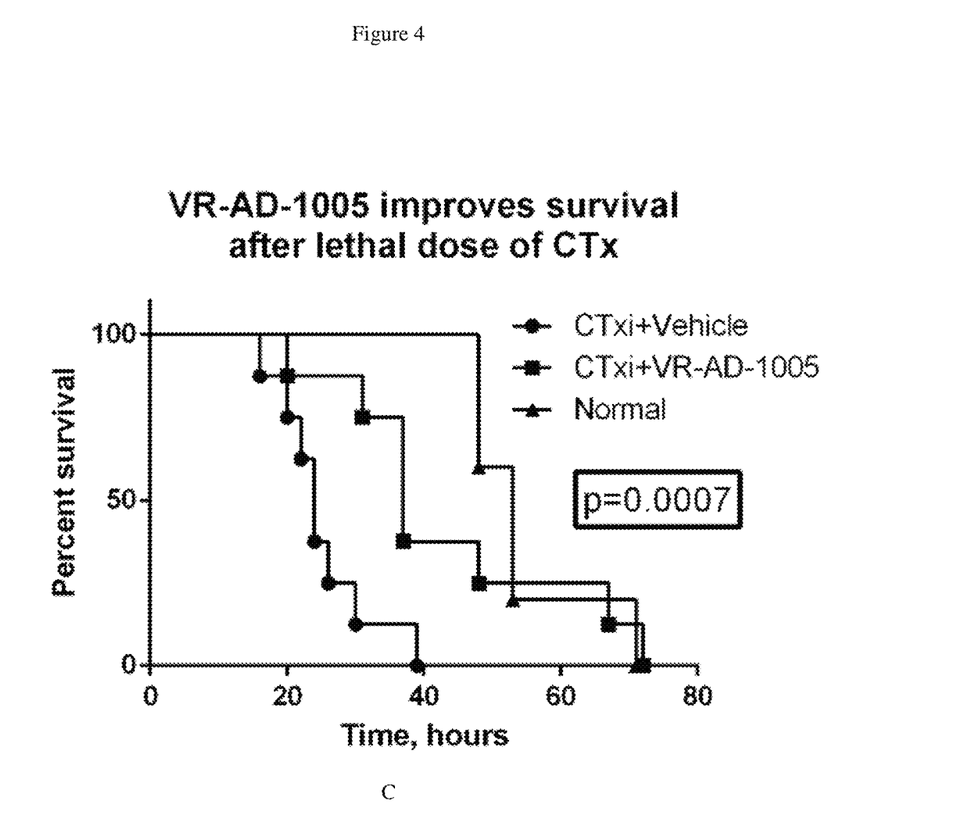
FIG. 4 presents data showing that an exemplary composition, VR-AD-1005, significantly improves survival in mice after lethal dose of CTx.

Intestinal secretion elicited by the cholera toxin (CTx, FIG. 3, grey bar) was reduced by 70% after administration of VR-AD-1005, prepared as above (CTx+VR-AD-1005, FIG. 3, black bar). If administered individually, neither polyphenol nor sucralfate reduced the volume of intestinal secretion (sucralfate, diagonal shading and polyphenol, horizontal shading) indicating synergistic effect of the combination VR-AD-1005. The results are shown in FIG. 3. In our model of severe cholera, a single dose of our drug has shown both the ability to reduce the volume of intestinal secretion elicited by the overdose of cholera toxin by more than 70% (FIG. 3) and the ability to reduce mortality following a lethal dose of cholera toxin by more than 30% (FIG. 4).

Example 7

One embodiment of a general reaction sequence for preparation of the substance:

Dissolve or dilute acid in water to a desired concentration (10-100% for citric acid, 0.1-2M for HCL)

Dissolve or dilute polyphenol in the acid solution by stirring at room temperature, to form an acid-polyphenol solution.

Dissolve sucralfate in the acid-polyphenol solution.

Incubate with stirring/mixing until complete dissolution of sucralfate and formation of a uniform gel or liquid (30 min-2 hours). Color change can be observed.

Dry resulting gel or liquid. Pulverize.

Dissolve resulting powder in water.

Administer to experimental animals or cells.

Example 8

The following compositions, prepared as described above, have been tested by oral administration and/or intestinal loop injections in the mouse models of cholera-toxin induced diarrhea: (Dried sloe berry extract)-sucralfate-citric acid in the w/w ratio of 0.5/1/1.2 administered at 50 mg/ml, 100 microliters per animal by gavage.

Tannic acid-sucralfate-citric acid in the w/w ratio of 0.1/1/0.5 administered at 100 mg/ml, 100 microliters per animal by gavage.

Gallic acid-sucralfate-citric acid in the w/w ratio of 0.1/1/0.5 administered at 100 mg/ml, 100 microliters per animal by gavage.

All compositions demonstrated reduction in the secretion of intestinal fluid in response to 20 microgram cholera toxin challenge. In the case of (dried sloe berry extract)-sucralfate-citric acid, the mean fluid secretion was 4.663±0.2313 N=3, p=0.0019. In the case of tannic acid-sucralfate-citric acid, mean fluid secretion was 6.473±0.5885 N=3, p=0.0185. In the case of gallic acid-sucralfate-citric acid, mean fluid secretion was 5.727±0.4480 N=3, p=0.0068. In the case of control (phosphate-buffered saline) mean fluid secretion was 9.853±0.7188 N=4. Observed anti-diarrheal effect via reduction in the volume of fluid secreted in response to cholera toxin challenge.

Example 9

The following compositions have been tested by oral administration in mouse models of chemotherapy-induced intestinal mucositis using 5-fluorouracil for mucositis induction: (Dried extract of sloe berry-blueberry mixture)-sucralfate-citric acid in the ratio of 0.5/1/1.2 and 0.1/1/0.24. Before administering the treatment, the mice were treated for 3 days with 50 mg/kg 5-fluorouracil. Dosage calculations were made daily depending on weight of each mouse. At day 4 mice started receiving oral gavage of (dried extract of sloe berry-blueberry mixture)-sucralfate-citric acid in the above ratios at 50 mg/ml, 100 microliters per animal once per day was added to the treatment plan. Phosphate buffered saline 100 microliters per animal once per day was used as control. At day 4 of treatment, there was a 25% recovery of weight loss due to 5-fluorouracile treatment in the control group, while both treatment groups with (Dried extract of sloe berry-blueberry mixture)-sucralfate-citric acid in the ratio of 0.5/1/1.2 and 0.1/1/0.24 demonstrated complete weight recovery and 64% and 23% weight gain in comparison with the mass lost due to 5-fluorouracil treatment.

Example 10

The following compositions have been tested in mouse models of 5% dextran sulfate sodium-induced inflammatory bowel disease by oral or rectal administration: (Dried sloe berry extract)-sucralfate-citric acid in the w/w ratio 0.05/0.4/1 (VR-AD-2005).

Inflammatory bowel disease was induced by administering 5% DSS in drinking water for 5 days to C57BL6 mice. Co-administration of (dried sloe berry extract)-sucralfate-citric acid formulations by gavage for 5 days reduced diarrheal incidence and severity.

Figure 5:
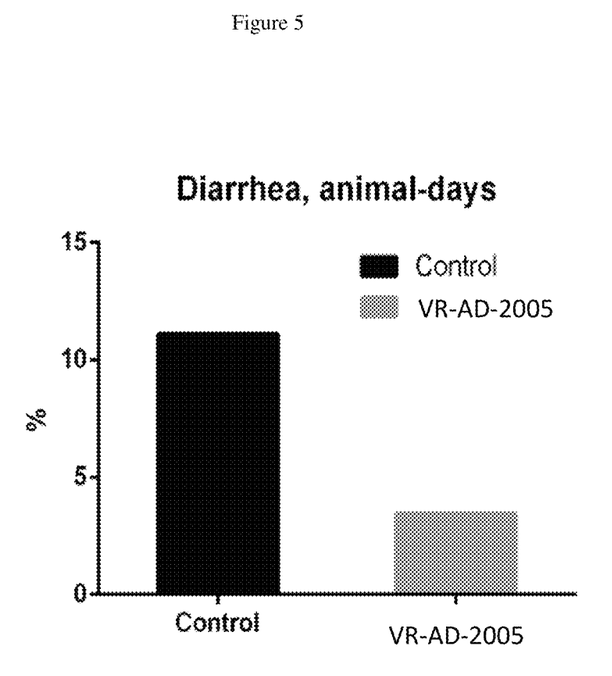
FIG. 5 presents data showing the reduction of diarrheal episodes after non-lethal, 96-hour 5% DSS challenge in mice by an exemplary composition (VR-AD-2005) against a comparative control.
Figure 6:
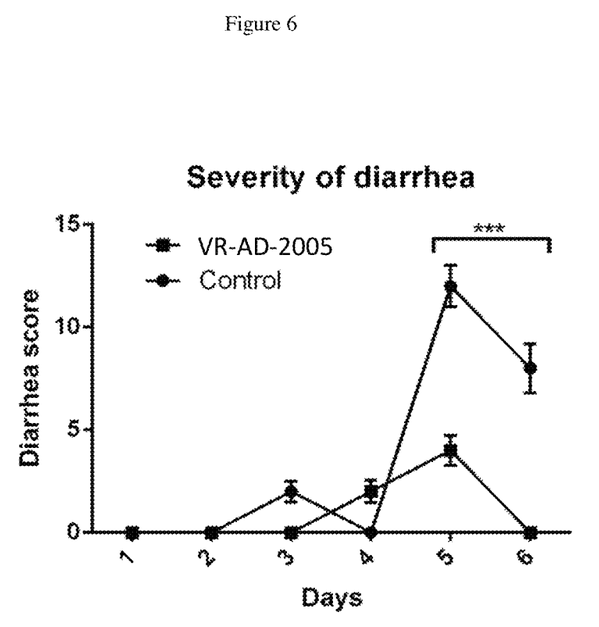
FIG. 6 presents data showing the reduction of diarrheal severity after non-lethal, 96-hour 5% DSS challenge in mice by an exemplary composition (VR-AD-2005) against a comparative control.

Non-lethal (96-hour) 5% DSS challenge data from mice are shown in FIGS. 5 and 6. Treatment period with pH 2.5 (dried sloe berry extract)-sucralfate-citric acid hydrogel (VR-AD-2005), administered for 5 days, is shown. Diarrheal frequency was expressed as percent of symptomatic days over the total number of days in the treatment period. For diarrhea severity, diarrhea was scored as 0 (normal stool), 2 (soft stool) or 4 (liquid stool), and both the number of diarrheal episodes and the severity were factored in severity of diarrhea calculations.

What is claimed is:

1. A composition, comprising a reaction product of: one or more polyphenol compound; sucralfate; and at least one acid; wherein the polyphenol is sourced from one or more of blueberry, bilberry, sloe, chokeberry, blackcurrant, dried form thereof, seed form thereof, juice thereof, powder form thereof, liquid form thereof, extract thereof, or combination thereof.

2. The composition of claim 1, wherein the polyphenol is a mixture of sloe and blueberry, mixture of sloe and bilberry, dried form thereof, seed form thereof, juice thereof, powder form thereof, liquid form thereof, extract thereof, or combination thereof.

3. The composition of claim 1, wherein the polyphenol is one or more of gallic acid, hydrolysable gallic acid, non-hydrolyzable gallic acid, condensed gallic acid, phlorotannin, cyanidin, delphinidin, petunidin, pelargonidin, peonidin, malvidin, catechin, gallocatechin, epicatechin, epigallocatechin, quercetin, tannic acid, apigenin, penta-m-digalloyl glucose, tannin, condensed tannin, gallotannic acid, gallotannin, tanninium, monomeric form thereof, polymer thereof having degree of polymerization of 1, 2 or more, glycosylated form thereof, aglycone form thereof, salt thereof, ester thereof, or combination thereof.

4. The composition of claim 1, wherein the polyphenol is tannic acid, gallic acid, salt thereof, or combination thereof.

5. The composition of claim 1, wherein the acid is selected from the group consisting of citric acid, HCl, malic acid, tartaric acid, succinic acid, oxalic acid, benzoic acid, isocitric acid, quinic acid, fumaric acid, acetic acid, lactic acid, fruit acid, and combinations thereof.

6. The composition of claim 1, wherein the acid is selected from the group consisting of citric acid, malic acid, tartaric acid, succinic acid, oxalic acid, or any combination thereof.

7. The composition of claim 1, wherein the acid is selected from the group consisting of HCl, citric acid, malic acid, and combinations thereof.

8. The composition of claim 1, wherein an acid/polyphenol/sucralfate weight ratio is acid 0.0001-1:polyphenol 0.001-1:sucralfate 0.0001-1.

9. The composition of claim 1, wherein an acid/polyphenol/sucralfate weight ratio is acid 0.001-0.5:polyphenol 0.002-0.5:sucralfate 0.0001-0.5.

10. The composition of claim 1, wherein an acid/polyphenol/sucralfate weight ratio is acid 0.1-1:polyphenol 0.05-0.5:sucralfate 0.01-1.

11. The composition of claim 1, further comprising an active or anti-diarrheal selected from the group consisting of loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

12. The composition of claim 1, which is in the form of a hydrogel.

13. A method for making the composition of claim 1, comprising:
 contacting one or more polyphenol compound, sucralfate, and at least one acid; and
 reacting, to form a reaction product;
 wherein the polyphenol and sucralfate are contacted first with each other, and then with the acid;
 or wherein the sucralfate and acid are contacted first with each other, and reacted, and then contacted and reacted with the polyphenol.

14. A method for treating a diarrheal disease, comprising administering to a subject needing such treatment or at risk of needing such treatment, the composition of claim 1.

15. A method for treating a diarrheal disease, comprising administering to a subject needing such treatment or at risk of needing such treatment, the composition of claim 1; and at least one active or anti-diarrheal selected from the group consisting of loperamide, racecadotril, alosetron, cholestyramine, crofelemer, atropine, diphenoxylate, bismuth subsalicylate, antibody, antibody fragment-targeting toxins, antibody fragment-targeting signaling molecule-inducing diarrheal disease, peptide, antisecretory peptide, antibiotic, non-absorbable antibiotic, ion channel inhibitor, agent acting at the surface elements of intestinal cell, or combination thereof.

* * * * *